(12) United States Patent
Hasegawa et al.

(10) Patent No.: US 8,184,930 B2
(45) Date of Patent: May 22, 2012

(54) TITANIA NANOTUBE AND METHOD FOR PRODUCING SAME

(75) Inventors: Akira Hasegawa, Tsukuba (JP); Kazuyuki Hirao, Kyoto (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 437 days.

(21) Appl. No.: 10/553,196

(22) PCT Filed: Apr. 8, 2004

(86) PCT No.: PCT/JP2004/005081
§ 371 (c)(1),
(2), (4) Date: Oct. 13, 2005

(87) PCT Pub. No.: WO2004/092072
PCT Pub. Date: Oct. 28, 2004

(65) Prior Publication Data
US 2006/0193766 A1    Aug. 31, 2006

(30) Foreign Application Priority Data

Apr. 15, 2003 (JP) ................................ 2003-109968

(51) Int. Cl.
*C01G 23/047* (2006.01)
*G02B 6/00* (2006.01)

(52) U.S. Cl. .......... 385/12; 423/610; 428/398; 435/807; 435/808

(58) Field of Classification Search .................. 977/811; 423/610; 428/398; 435/807, 808; 385/12
See application file for complete search history.

(56) References Cited

U.S. PATENT DOCUMENTS

| | | | |
|---|---|---|---|
| 6,027,775 A | 2/2000 | Kasuga et al. | |
| 6,537,517 B1 | 3/2003 | Kasuga et al. | |
| 2005/0255315 A1 | 11/2005 | Yamanaka et al. | |

FOREIGN PATENT DOCUMENTS

| | | |
|---|---|---|
| JP | 47-2430 B | 1/1971 |
| JP | 01-28692 A | 11/1989 |
| JP | 07-2598 A | 1/1995 |
| JP | 07-242422 A | 9/1995 |
| JP | 10-152323 A | 6/1998 |
| JP | 2000-203998 A | 7/2000 |
| JP | 2002-241129 A | 8/2002 |
| JP | 2003/34531 A | 2/2003 |
| WO | 2004/057064 | 7/2004 |
| WO | 2004/057064 A1 | 7/2004 |

OTHER PUBLICATIONS

Craig A. Grimes, "A Sentinel Sensor Network for Hydrogen Sensing", Feb. 21, 2003, Sensors, 3, 69-82.*
Zhu et al., "Sonochemical synthesis of titania whiskers and nanotubes", *Chem. Communication*, pp. 2616-2617 (2001).
Hirao, "Preparation of Long Fibrous Titanium Oxide Nanotube", *Journal of Materials Science Society of Japan*, 52:16-17 (May 16, 2003), English Translation.
Ito et al., "Preparation of Undirectionally Oriented $TiO_2$ Tubes by Electrostatic Method", *Journal of the Institutes of Electrostatics*, pp. 265-266 (2000), English Translation.
Yang et al., "Eggshell Membrane Templating of Hierachically Ordered Macroporons Networks Composed of $TiO_2$ Tubes", *Adv. Mater.*, 14(21):1543-1546 (Nov. 4, 2002).
T. Kasuga et al., "Formation of Titanium Oxide Nanotube", Langmuir 1998, 14, pp. 3160-3163.
T. Kasuga et al., "Titania Nanotubes Prepared by Chemical Processing", Advanced Materials, 1999, 11, No. 15, pp. 1307-1311.
Hidenori Nakamura et al., "Silica Gel Nanotubes obtained by the Sol-Gel Method", J. Am. Chem. Soc., 117:2651-2652 (1995).

* cited by examiner

*Primary Examiner* — Wayne Langel
(74) *Attorney, Agent, or Firm* — Sughrue Mion, PLLC

(57) ABSTRACT

A titania nanotube suitable as an optical sensor or gas sensor is provided. The titania nanotube has a length of 1 µm or more; preferably a diameter of 0.1 µm or less and an aspect ratio of 100 or more.

15 Claims, No Drawings

TITANIA NANOTUBE AND METHOD FOR PRODUCING SAME

FIELD OF THE INVENTION

The present invention relates to a titania nanotube and a method for producing the same.

DESCRIPTION OF BACKGROUND ART

From finding of a titania nanotube, a possibility of producing a nanotube has been investigated on various substances. As a result, production of a nanotube made of titania ($TiO_2$) is confirmed. Titania is one of substances having a photocatalyst activity, and titania in the form of nanotube has a higher photocatalyst activity as compared with that in the form of powder, consequently, various application thereof are expected.

As such a titania nanotube, for example, that having a diameter of from 5 to 80 nm and a length of from 50 to 150 nm is known (Japanese Patent Application Laid-Open (JP-A) No. 10-152323).

However, the titania nanotube described in the publication is not satisfactory for use as an optical sensor and gas sensor.

Under such conditions, the present inventors have intensively studied to develop a titania nanotube suitable as an optical sensor or gas sensor and resultantly completed the present invention. Further, the present inventors have intensively studied also a method for producing a titania nanotube, leading to completion of the present invention.

Namely, the present invention provides a titania nanotube having a length of 1 μm or more.

The present invention provides also a sensor having a titania nanotube having a length of 1 μm or more and an electrode in which the titania nanotube and the electrode are connected.

Further, the present invention provides a method for producing a titania nanotube, comprising a step of dispersing a titania powder in a sodium hydroxide aqueous solution at a temperature of 60° C. or more.

The titania nanotube provided by the present invention is used also as a reinforcing material for metal and resin, in addition to optical sensors and gas sensors. The sensor of the present invention using this titania nanotube may be used for monitoring the condition of plants in the machine industry and chemical industry. Further, according to the production method of the present invention, such a titania nanotube can be obtained easily.

DESCRIPTION OF EMBODIMENTS OF THE INVENTION

The titania nanotube of the present invention has a length of 1 μm or more. The titania nanotube has a length of preferably 10 μm or more, further preferably 100 μm or more from the standpoint of handling and working. On the other hand, though the upper limit of length is not particularly restricted, it is usually 50 mm or less, preferably 10 mm or less.

The titania nanotube of the present invention has a section usually in the form of circle, and its diameter is preferably 0.1 μm or less. Though the lower limit of diameter is not particularly restricted, it is usually 5 nm, preferably 8 nm. When a titania nanotube having small diameter is used as a sensor, its detection sensitivity increases preferably, and when used as a reinforcing material for metal and resin, an effect of reinforcing a matrix increases preferably. Though the reason for increase in the sensitivity of a sensor is not definite, it is guessed that because of small diameter, the specific surface area of the titania nanotube increases, and change of the condition of the surface or internal surface of the titania nanotube exerts an influence. Though the reason for increase in the reinforcing effect is also not definite, it is guessed that a tendency of mutual entangling of titania nanotubes exerts an influence.

The titania nanotube of the present invention has an aspect ratio preferably of 100 or more. On the other hand, the upper limit of the aspect ratio is not particularly restricted and it is usually about $10^8$, preferably about 10000. The aspect ratio is a ratio L/D of a length L along the longitudinal direction to the maximum width D (diameter when cross section is circle) of a titania nanotube.

The titania nanotube of the present invention is used also as a photocatalyst, ultraviolet absorbing and shielding agent, sunburn preventive, material for photo-electric cell, electrically conductive filler, bone filling material and the like, in addition to sensors and reinforcing materials.

The sensor of the present invention has a titania nanotube having a length of 1 μm or more and an electrode (this electrode is connected at one end with a controlling apparatus outside and plays a role of transmitting electrical change of a titania nanotube) wherein the titania nanotube and the electrode are connected. Examples of the sensor include photo-sensors such as an ultraviolet sensor, infrared sensor and visible sensor, and gas sensors. With an optical sensor, the electric property (electric conductivity) of a titania nanotube changes depending on the light irradiation flux, therefore, the light irradiation flux is obtained by measuring this change. With a gas sensor, the electric property (electric conductivity) of a titania nanotube changes by adsorption of molecules of a specific gas in the titania nanotube, therefore, the gas concentration is obtained by measuring this change.

As the electrode connected to a titania nanotube, for example, wires made of gold, platinum or silver may be used.

The method for producing a titania nanotube of the present invention comprises a step of dispersing a titania powder in a sodium hydroxide aqueous solution.

Examples of the titania powder used for production include titanium oxides ($TiO_2$) of rutile type or anatase type. The titania powder has an average particle diameter of preferably about 50 nm or less, more preferably about 20 nm or less, further preferably about 10 nm or less. On the other hand, though the lower limit of the average particle diameter is not particularly restricted, the lower limit thereof is usually about 3 nm, preferably about 6 nm. The average particle size in this case is represented by the corresponding equivalent particle diameter calculated from BET specific surface area, and may be advantageously calculated from the specific gravity ($g/cm^3$) of a titania powder and its BET specific surface area ($m^2/g$) according to the following formula:

$$6/[\text{BET specific surface area} \times \text{specific gravity}]$$

The sodium hydroxide aqueous solution has a concentration of sodium hydroxide of usually about 1 M (mol/liter) or more, more preferably about 3 M or more, more preferably about 7 M or more, and usually about 15 M or less, preferably about 13 M or less, more preferably about 12 M or less.

Regarding the weight ratio of a sodium hydroxide aqueous solution to a titania powder, the proportion of a titania powder is usually about 0.01 part by weigh or more, and usually about 0.1 part by weigh or less, preferably about 0.04 part by weight, based on 100 parts by weight of a sodium hydroxide aqueous solution.

Dispersion is conducted at a temperature of 60° C. or more. The temperature of a sodium hydroxide aqueous solution in dispersing is preferably about 90° C. or more, more preferably about 100° C. or more, and preferably about 120° C. or less. The dispersion time is usually about 1 hour or more and about 50 hours or less. Dispersion may be advantageously conducted under normal pressure (about 0.08 MPa or more and about 0.12 MPa or less) or under reduced pressure (less than about 0.08 MPa).

Dispersion may be advantageously conducted usually by stirring or irradiation with an ultrasonics, preferably by stirring. Specifically, dispersion may be advantageously conducted by a method in which a titania powder and a sodium hydroxide aqueous solution are placed in a vessel with a stirrer, and the mixture in the vessel is stirred or a method in which a titania powder and a sodium hydroxide aqueous solution are mixed and this mixture is irradiated with an ultrasonics, or by a method combining them.

Dispersion may be conducted either in a vessel open to air or a sealed vessel. When dispersion is conducted under high water vapor partial pressure of a sodium hydroxide aqueous solution, it is preferable to use an open vessel and to conduct an operation of returning water vapor by reflux or to use a pressure-resistant sealed vessel.

Titania obtained by dispersion is usually cooled to room temperature, then, separated from a sodium hydroxide aqueous solution. Separation may be advantageously conducted by filtration, decantation and the like. It is preferable to wash the separated titania. Washing may be advantageously conducted, for example, by a method in which titania is mixed with an inorganic acid such as hydrochloric acid or nitric acid to neutralize sodium hydroxide remaining in titania, then, this slurry is subjected to solid-liquid separation (filtration, decantation and the like), and the resulted solid is re-pulped in water.

The washed solid may be further heated in air after drying. By these operations, the crystallinity of a titania nanotube can be enhanced.

EXAMPLES

The present invention will be illustrated by examples below but the scope of the invention is not limited to these examples.

Example 1

One hundred parts by weight of a 10 M sodium hydroxide aqueous solution and 0.0187 parts by weight of a titania powder (manufactured by Tayca Corporation, rutile type, average particle diameter: 10 nm) were placed in a PTFE vessel. The mixture in the vessel was heated up to 110° C. and maintained at 110° C. for 20 hours while stirring with a magnetic stirrer.

After maintaining, the mixture in the vessel was placed in a centrifugal sedimentation tube, solid was precipitated by centrifugal sedimentation, then, the supernatant was removed. Distilled water was added in the centrifugal sedimentation tube and mixed, then, solid was precipitated by sedimentation, thus, solid was washed.

The resulted solid and 0.1 N nitric acid were mixed, solid was precipitated by centrifugal separation, the supernatant was removed, then, this solid and distilled water were mixed, then, the solid was precipitated, and the supernatant was removed, and this operation was repeated until pH of the supernatant reached 7, to obtain a titania nanotube.

The titania nanotube was observed by SEM (manufactured by Hitachi, Ltd, H-510 type) and TEM (manufactured by Hitachi, Ltd, H-9000 type). The titania nanotube had a length of 120 µm, a diameter of 50 nm and an aspect ratio of 2400.

Example 2

The same operation was conducted as in Example 1 except that a titania powder (manufactured by Ishihara Sangyo Kaisha, LTD., anatase type, average particle diameter: 6 nm) was used as the raw material titania powder. The resulted titania nanotube had a length of 120 µm, a diameter of 50 nm and an aspect ratio of 2400.

Comparative Example 1

The same operation was conducted as in Example 1 except that potassium hydroxide was used instead of sodium hydroxide. The resulted solid was in the form of particle and a titania nanotube was not formed.

The invention claimed is:

1. A titania nanotube having a length of 10 µm or more.
2. The titania nanotube according to claim 1 wherein the diameter is 0.1 µm or less.
3. The titania nanotube according to claim 1 or 2 wherein the aspect ratio is 100 or more.
4. A sensor having the titania nanotube according to claim 1 or 2 and an electrode in which the titania nanotube and the electrode are connected.
5. A sensor having the titania nanotube according to claim 3 and an electrode in which the titania nanotube and the electrode are connected.
6. A method for producing a titania nanotube, comprising a step of dispersing a titania powder in a sodium hydroxide aqueous solution at a temperature of 60° C. or more so as to form a titania nanotube having a length of 10 µm or more.
7. The method according to claim 6 wherein the titania powder has an average particle diameter of 50 nm or less.
8. The method according to claim 6 or 7 wherein the amount of the titania powder is 0.01 part by weight or more and 0.1 part by weight or less based on 100 parts by weight of a sodium hydroxide aqueous solution.
9. The method according to claim 6 or 7, wherein the sodium hydroxide aqueous solution has a concentration of sodium hydroxide of 1 M or more and 15 M or less.
10. The method according to claim 9 wherein the sodium hydroxide aqueous solution has a concentration of sodium hydroxide of 3 M or more and 13 M or less.
11. The method according to claim 10 wherein the sodium hydroxide aqueous solution has a concentration of sodium hydroxide of 7 M or more and 12 M or less.
12. The method according to claim 6, wherein dispersion is conducted at 90° C. or more and 120° C. or less.
13. The method according to claim 6, wherein dispersion is conducted by stirring or irradiation with an ultrasonics.
14. The method according to claim 13 wherein dispersion is conducted by stirring.
15. The method according to claim 8, wherein the sodium hydroxide aqueous solution has a concentration of sodium hydroxide of 1 M or more and 15 M or less.

* * * * *